United States Patent [19]

Robertson et al.

[11] Patent Number: 4,892,712

[45] Date of Patent: Jan. 9, 1990

[54] FLUID PURIFICATION

[75] Inventors: Michael K. Robertson; Robert B. Henderson, both of London, Canada

[73] Assignee: Nutech Energy Systems Inc., London, Canada

[21] Appl. No.: 94,000

[22] Filed: Sep. 4, 1987

[51] Int. Cl.⁴ .......................... B01J 1/10; B01J 19/08; G01N 21/01; G01N 21/51

[52] U.S. Cl. ................................ 422/186; 422/186.3; 422/905; 422/24; 261/DIG. 42; 250/431; 250/436; 250/437; 250/438; 210/748; 210/763; 210/510.1; 204/157.44; 204/157.15; 204/903

[58] Field of Search ...................... 422/186.3, 905, 24, 422/186; 250/436, 437, 438, 931; 210/748, 760, 764, 510.1, 763; 204/157.44, 157.15, 903

[56] References Cited

U.S. PATENT DOCUMENTS

| | | | |
|---|---|---|---|
| 3,067,115 | 12/1962 | Clingman, Jr. | 422/186.3 X |
| 3,846,072 | 11/1974 | Patterson | 250/438 X |
| 4,346,131 | 8/1982 | Yoldas | 428/35 |
| 4,446,236 | 5/1984 | Clyde | 422/186.3 X |
| 4,615,799 | 10/1986 | Mortensen | 250/438 X |
| 4,694,179 | 9/1987 | Lew et al. | 422/186.3 X |

OTHER PUBLICATIONS

"Photooxidation of Organic Impurities in Water Using Thin Films of Titanium Dioxide" by Ralph W. Matthews–published in J. Phys. Chem. 1987, 91, 3328-3333.

"Heterogeneous Photocatalysis: Degradation of Dilute Solutions of Dichloromethane ($CH_2Cl_2$), Chloroform ($CHCl_3$), and Carbon Tetrachloride ($CCl_4$) with Illuminated $TiO_2$ Photocatalysts" by Chen-Yung Hsiao, et al–Journal of Catalysis 82, 1983, pp. 418-423.

"Photocatalysis Over $TiO_2$ Supported on a Glass Substrate" by Nick Serpone, et al–Solar Energy Materials 14 (1986) pp. 121-127, Elsevier Science publishers B.V.–North-Holland Physics Publishing Divisions, Amsterdam.

"Integrated Chemical Systems: Photocatalysis at $TiO_2$ Incorporated into Nafion and Clay" by Fu-Ren F. Fan, et al–The Journal of Physical Chemistry 1985, 89, 4418-4420.

"Use of Sol-Gel Thin Films in Solar Energy Applications" by R. B. Pettit, et al–published in Solar Energy Materials 14 (1986) 269-287.

"Sol-Gel Derived Antireflective Coatings for Silicon" by C. J. Brinker et al–published in Solar Energy Materials 5 (1981) 159-172.

"Oxide Layers Deposited from Organic Solutions" by H. Schroeder.

"Hydrolysis of Titanium Alkoxide and Effects of Hydrolytic Polycondensation Parameters" by B. E. Yoldas–published in the Journal of Materials Science 21 (1986) 1087-1092.

"Photooxidation of Organic Impurities in Water Using Thin Films of Titanium Dioxide" by Ralph W. Matthews–published in the Journal of Physical Chemistry 1987, 91, 3328-3333.

"Solar-Electric Water Purification Using Photocatalytic Oxidation with TiOhd 2 as a Stationary Phase" by Ralph W. Matthews–published in Solar Energy vol. 38, No. 6, pp. 405-413, 1987.

"Photodechlorination of PCB's in the Presence of Titanium Dioxide.in Aqueous Suspensions" by John H. Carey, et al–Bulletin of Environmental Contamination & Toxicology, vol. 16, No. 6, pp. 697-701, 1976 Springer-Verlag New York Inc.

"Hydroxylation Reactions Induced by Near-Ultraviolet Photolysis of Aqueous Titanium Dioxide Suspensions" by Ralph W. Matthews.
J. Chem. Soc. Faraday Trans. 1, 1984, 80, pp. 457-471.

"Carbon Dioxide Formation from Organic Solutes in Aqueous Suspensions of Ultraviolet-Irradiated $TiO_2$, Effect of Solute Concentrations" by Ralph W. Matthews Aust. J. Chem., 1987, 40,001-000, pp. 1-9.

Primary Examiner—Howard J. Locker

[57] ABSTRACT

A purifier for water or air removes, reduces or detoxifies organic pollutants therefrom by causing the fluid to contact a matrix having surfaces with which a fixed anatase ($TiO_2$) or other photoreactive metal semiconductor material is bonded, in the presence of light of a wavelength that will activate the material.

28 Claims, 2 Drawing Sheets

FLUID PURIFICATION

FIELD OF THE INVENTION

This invention relates to the purification of a fluid, for example water or air, and more particularly to the removal, reduction or detoxification from water or air of organic pollutants, such as polychlorobiphenyls (PCB's), trihalomethanes, benzene derivatives, pesticides and others, some of which are mentioned below.

PRIOR ART

It has been known for some time that titanium dioxide can achieve photodechlorination of PCB's, as described by J. H. Carey et al in "Photodechlorination of PCB's in the Presence of Titanium Dioxide in Aqueous Suspensions", Bulletin of Environmental Contamination & Toxicology, Vol 16, No. 6, pp. 697–701, 1976 Springer-Verlag New York Inc. Carey et al describe irradiation by ultra violet light with a wavelength of 365 nm of a 25 ppb aqueous solution of Aroclor 1254* in the presence of suspended particulate titanium dioxide After 30 min. no unreacted Aroclor could be detected in solution or adsorbed on the surface of the $TiO_2$. Similar experiments were conducted with other PCB's and resulted in an observed disappearance of the chlorinated biphenyls and the production of chloride ions.

*Trade Mark

R. W. Matthews has reported the conversion (often called "mineralization") of a number of organic compounds to carbon dioxide by exposure to near ultra violet light in aqueous suspensions of anatase, a form of crystalline titanium dioxide. The solutes studied were benzene, benzoic acid, benzoate ion, salicylate ion, phenol, chlorobenzene, aniline, anilinium ion, nitrobenzene, chloroform and formic acid ("Carbon Dioxide Formation from Organic Solutes in Aqueous Suspensions of Ultraviolet-Irradiated $TiO_2$. Effect of Solute Concentration" by R. W. Matthews, Aust. J. Chem., 1987, 40,001–000, pp 1–9). The same author had earlier reported similar results with benzoic acid or sodium benzoate ("Hydroxylation Reactions Induced by Near Ultraviolet Photolysis of Aqueous Titanium Dioxide Suspensions," J. Chem. Soc. Faraday Trans. 1, 1984, 80, pp 457–471).

Chen-Yung Hsiao et al have also reported the mineralization of chloromethanes to $CO_2$ and HCl by the heterogeneous photocatalyst $TiO_2$ ("Heterogeneous Photocatalysis:Degradation of Dilute Solutions of Dichloromethane ($CH_2Cl_2$), Chloroform ($CHCl_3$), and Carbon Tetrachloride ($CCl_4$) with Illuminated $TiO_2$ Photocatalyst," Journal of Catalysis 82, 1983, pp 418–423).

Similar reactions have not been limited to $TiO_2$. Other metal semiconductors, such as ZnO, CdS, $WO_3$ and $SnO_2$, have been utilized in photocatalytic processes for the degradation of environmental contaminants ("Photocatalysis Over $TiO_2$ Supported On A Glass Substrate," by N. Serpone et al, Solar Energy Materials 14(1986) pp 121–127, Elsevier Science Publishers B.V.-North-Holland Physics Publishing Divisions, Amsterdam).

SUMMARY OF THE INVENTION

The object of the present invention is to adapt this previously observed laboratory reaction to a practical fluid purification system for either commercial or domestic use, e.g. for the purification of potable water or for treating industrial wastes or environmental spills, or for removing pollutants from air.

Most of the laboratory reactions discussed in the literature referred to above involve forming a suspension of particulate $TiO_2$ (or other metal semiconductors) in the water containing the organic pollutants that are to be converted into harmless by-products. This procedure is impracticable for the commercial purification of water, because the particulate $TiO_2$ would have to be subsequently removed before the water could be used, and this would be either impossible or prohibitively expensive.

In its preferred form, the present invention solves this problem by firmly bonding the $TiO_2$ or other metal semiconductor (subsequently referred to as the "photoreactive material") with, to or into surfaces of a substrate that has the properties of a large surface area for coating with the photoreactive material, a porous construction such that the fluid to be treated can thoroughly contact the coated surfaces, and sufficient transparency to light at a wavelength to which the photoreactive material photoreacts to ensure that all the coated surfaces receive such light at an adequate energy level to ensure the catalytic or photoreactive effect.

The bonding of the photoreactive material to the substrate must be so firm that no appreciable amount of it enters the fluid.

The preferred form of base material for use as the substrate is a length of fiberglass mesh that has been wound into a cylindrical, multi-layer sleeve having a number of convolutions superposed on each other.

Fiberglass absorbs only a small percentage of the light at the wavelengths used, i.e. between 300 and 425 nm, and hence such mesh is substantially transparent. The sleeve is preferably such that the holes in the mesh of one convolution are oriented out of alignment in relation to the holes in the next convolution. Combined with the facts that a large proportion of a typical mesh is holes and that the strands absorb only a small amount of the light passing through them, such a non-aligned orientation enables the light to pass through multiple convolutions with relatively little attenuation. As a result, a sleeve of such mesh placed around a cylindrical lamp can have a large number of superposed convolutions without reducing to an unacceptable level the intensity of the light received by the photoreactive material coated on the outer convolution. This ability to use a multiple layer sleeve of mesh as a substrate to form a matrix greatly facilitates the achievement of a compact arrangement.

The mesh need not necessarily be wound into a sleeve. The convolutions referred to above can be replaced by superposed layers of any other physical shape, such as a series of concentric surfaces. For example, coated films could be rolled into coaxial tubes, or coated glass (e.g. sintered or porous glass) tubes of different diameters could be inserted within each other to yield a series of concentric surfaces. A single such tube can also be used. While the tube need not be porous, i.e. could be imperforate, there is the advantage of a porous tube or tubes in providing a larger surface area for the coating.

Moreover, the mesh need not necessarily be made of fiberglass. Any other assembly that is sufficiently transparent to the light can be used. Such an assembly can achieve its transparency either from its structure, e.g. a very open mesh, or from its own intrinsic property. For example, a material like stainless steel that is itself opaque to the light can be used, provided it has a sufficiently open structural form, i.e. the substrate as a whole is sufficiently transparent. What constitutes sufficient transparency of the substrate will depend on how many layers (convolutions) are superposed on one another. While the use of other materials is not precluded, fiberglass will normally be the preferred choice among currently available materials from the viewpoints of cheapness, light weight, convenience of handling, relatively high transparency and its inertness to the reactants.

Moreover, it is not essential to use a mesh. The invention is operable when the photoreactive material is in the form of a bonded coating on any suitable substrate.

Also, the substrate may take the form of filamentous fiberglass, i.e. non-woven insulation type material, or woven or spun glass wool, in which case the base material would not form distinct layers or convolutions but would simply constitute a loosely packed mass of fibers.

To ensure a clear understanding of the terminology adopted herein, it is to be noted that the term "base material" refers to the actual material itself, e.g. fiberglass; "substrate" refers to the assembly of this material, e.g. as a loose mass of fibers or as a mesh; while "matrix" refers to the combination of the substrate with the photoreactive material bonded therewith.

Assuming that anatase is the chosen photoreactive material, the preferred method of bonding it to the surfaces of the matrix is by an adaption of the known sol-gel technique. See, for example, "Use of Sol-Gel Thin Films in Solar Energy Applications" by R. B. Pettit et al, Solar Energy Materials 14(1986) pp 269–287, Elsevier Science Publishers B.V.-North-Holland Physics Publishing Division, Amsterdam.

As applied to the preferred form of the present invention, this bonding technique can involve the following steps.

A titanium alkoxide, e.g. ethoxide, dissolved in an organic solvent, e.g. anhydrous ethanol, is reacted with a controlled amount of an acid, e.g. nitric acid and water, to form a coating solution. Other methods can be adopted for forming a coating solution, the important feature of which is that it should contain a titanium alkoxide. The fiberglass mesh is then dipped into such a coating solution, the process being carried out in dry conditions. Subsequent exposure of the coated mesh to air results in a controlled hydrolysis process, i.e. causes setting of the polymer to yield an amorphous $TiO_2$ layer on the mesh surfaces. After a drying period, the coated mesh is fired at about 400° C. for about one hour, which converts the amorphous layer to the anatase crystal structure necessary for the photocatalytic reaction to proceed. The result is a very tight bonding of the anatase layer with, to or into the fiberglass strands, hence avoiding any measurable amount of the anatase entering the fluid to which the matrix will subsequently be exposed. This bonding may involve a covalent bonding between the substrate and the anatase.

Additional details of a bonding technique are given below.

As mentioned above, the invention is not limited to use with $TiO_2$. Other photoreactive metal semiconductors can replace the $TiO_2$, such as CdS, CdSe, $ZnO_2$, $WO_3$ and $SnO_2$.

The sol-gel technique can only be used to apply metal oxides. The non-oxide semiconductors must be applied by some other means, such as by vacuum or vapor deposition, electroplating or sintering. In this regard, it is important to note that sol-gel is the only one of these methods that is usable with non-flat surfaces. Consequently, sol-gel allows fabrication of the substrate in its final mechanical configuration before coating. With the non-oxide semiconductors, the method of manufacture must be changed. The base material will first have to be coated with the photoreactive semiconductor and then fabricated into a matrix.

Enhanced results can sometimes be achieved by doping the active material with a suitable dopant, e.g. platinum.

As indicated above, while the matrix can take a wide variety of physical forms, it is of substantial practical value to have a matrix that is of such a nature that it can readily be penetrated by the fluid, so that the latter comes into contact with substantially all the surfaces. To this end, it is desirable that the matrix encourage turbulent flow of the fluid through itself, a result that is well achieved by a rolled-up sleeve of fiberglass mesh.

Hence the invention, in one aspect, consists of a matrix for use in a method of removing, reducing or detoxifying organic pollutants from a fluid, comprising a porous substrate having a photoreactive metal semiconductor material bonded with, to or into surfaces of said substrate.

The substrate is preferably at least partially transparent to light at a wavelength to which the semiconductor material photoreacts.

The invention also consists of a method of removing, reducing or detoxifying organic pollutants from a fluid, comprising bringing such fluid into contact with a photoreactive metal semiconductor material bonded with, to or into surfaces of a substrate while subjecting such photoreactive material to light of wavelengths that activate said material.

The invention also consists of apparatus for carrying out this method.

Finally, in another aspect, the invention consists of a method of manufacturing a matrix for use in a method of treating organic pollutants from a fluid, said method comprising (a) preparing a coating solution containing a titanium alkoxide;

(b) coating surfaces of a base material with said coating solution to produce an amorphous layer of titanium dioxide on said surfaces; and (c) firing the coated base material at an elevated temperature to convert the amorphous layer to a layer of anatase bonded to the base material.

BRIEF DESCRIPTION OF THE DRAWINGS

A specific example of the invention is illustrated in the drawings, in which.

DETAILED DESCRIPTION OF PREFERRED EMBODIMENTS

Figure 1:
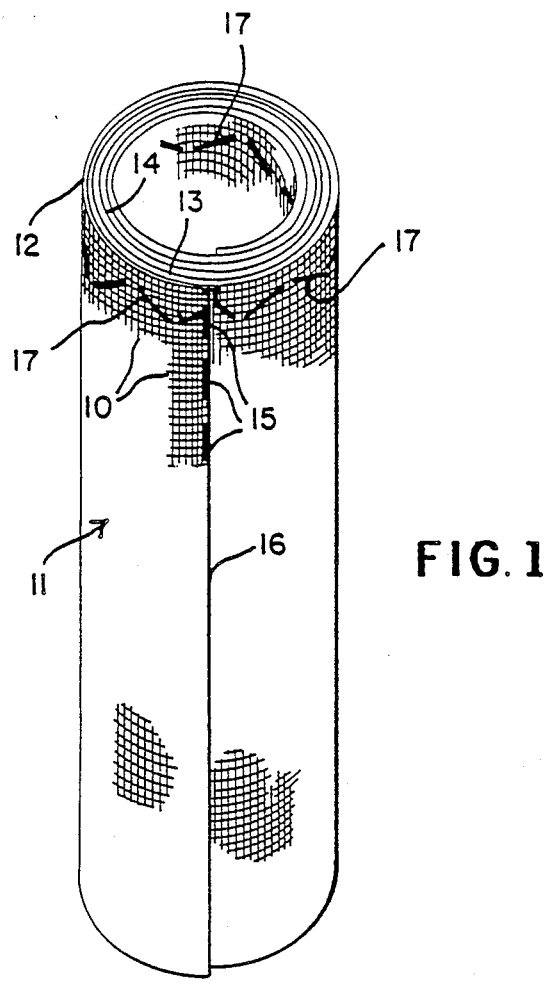
FIG. 1 is a perspective view of a matrix.

The matrix is a mesh substrate consisting of two transverse series of fiberglass strands 10 with, to or into which anatase or other photoreactive semiconductor material (not visible in the drawings) is bonded. This mesh is wound into a sleeve 11 to form superposed layers (convolutions) 12, 13, 14 etc. In a typical example, there could be between ten and twenty such convolutions, although this number can vary widely as circumstances require. An individual strand 15 threaded in an axial direction through a series of holes in the mesh serves to secure the end 16 of the outer convolution 12 to the next convolution 13 below. In addition, individual strands 17 are threaded circumferentially (preferably in a wavy fashion) around each convolution at each end of the sleeve and at its longitudinal centre (only the upper strand 17 is shown). These strands 17 act as spacers in serving to prevent the convolutions from lying too tightly against each other. In other words, they help to maintain the looseness and hence the porous property of the sleeve whereby water or air can flow along the matrix between the convolutions and thoroughly contact the coated surfaces. Obviously, other means can be used for securing the convolutions of the sleeve together while ensuring adequate spacing between them. For example, these strands 15 and 17 can be replaced by an inert, high temperature, inorganic adhesive applied as beads between strands 10.

The preferred method of bonding anatase to the fiberglass strands of a mes is as follows:

1. Preparation of Titanium (IV) Alkoxide Solution in Alcohol

Two solutions are prepared. In solution A, distilled water and 70% $HNO_3$ are mixed into anhydrous ethanol. In solution B, titanium (IV) ethoxide is dissolved in anhydrous ethanol. Solution B is added slowly to solution A with adequate stirring to ensure complete mixing of the solutions. The mole ratios (to titanium ethoxide, Solution B) are:

| Solution A: | | Solution B: | |
|---|---|---|---|
| water | 1.93 | titanium ethoxide | 1.00 |
| nitric acid | 0.02 | ethanol (ahydrous) | 40.6 |
| ethanol | 11.8 | | |

The above operations must be performed in a dry atmosphere, since exposure of the titanium ethoxide to water vapor will result in premature hydrolysis of the ethoxide. The final solution containing 30 gm/l of $TiO_2$ is aged overnight (about 16 hours) before being deposited on the base material.

2. Fiberglass Mesh Cleaning Procedure
   1. Heat in oven at 400° C. for one (1) hour
   2. Soak in 1% (weight/weight) NaOH solution at 85°-95° C. for 10 minutes
   3. Soak in 1N HCl at 40°-60° C. for 30–120 seconds
   4. Rinse with isopropyl alcohol
   5. Dry in oven at 100°-200° C. until ready to dip 3. Coating of Base Material The fiberglass mesh is dipped into the titanium alkoxide solution for approximately one (1) minute and withdrawn almost vertically at rates ranging from 20–80 cm/min. The coated material is dried at room temperature for 1-2 hours in a dust free environment before heat treatment.

4. Heat Treatment

The coated material is treated at 400° C. as follows:
Heating rate=room temperature to 400° C. in 2-5 hours
Soak time=1 hour at 400° C.
Cooling rate=400° C. to room temperature in 5 hours or more While the foregoing process has been found effective, many variations are possible. In particular, it has been found that the soaking temperature will vary with the amount of acid, and therefore a temperature within the range of 350° to 600° C. may be used.

Figure 2:
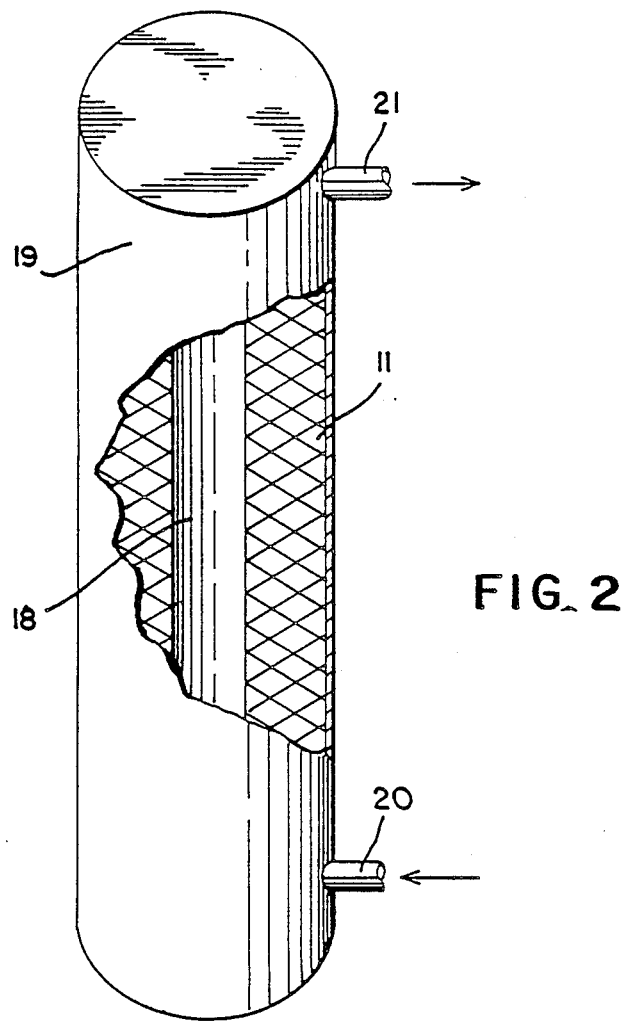
FIG. 2 shows an example of how such a matrix can be used in practice.

FIG. 2 shows diagrammatically how the sleeve 11 can be mounted around a cylindrical lamp 18 inside a cylindrical jacket 19 (conveniently, but not necessarily, of stainless steel) having an inlet 20 for polluted fluid and an outlet 21 for the treated fluid from which the pollutants have been substantially eliminated by conversion to harmless by-products.

The device in which the matrix carrying the fixed photoreactive material is caused to be contacted by the fluid can vary widely in size, shape, and general arrangement.

The lamp will be such as to emit light with wavelengths less than 425 nm, preferably peaking at 340–350 nm. It is notable that this range of wavelengths is present in the sunlight that reaches the surface of the earth, which opens up the possibility of dispensing with the lamp in locations where a source of power is unavailable. This result could be achieved by making the jacket 19 of a material transparent to light at these wavelengths, or otherwise arranging to expose the photoreactive material to sunlight in the presence of the water to be purified.

Such a transparent jacket could also be used in an arrangement in which one or more lamps are located outside the jacket.

In addition to the conversion of organic pollutants to carbon dioxide, and other harmless by-products, the light may simultaneously achieve some antibacterial function. Conventional ultra violet sterilizers use wavelengths around 250 nm, because this is the so-called germicidal wavelength at which the two strands of the DNA helix become locked together to prevent the bacteria reproducing. However, at the longer wavelengths used in the present invention, e.g. between 300 and 425 nm, and given a sufficient intensity of light, the bacteria can be expected to experience direct destruction.

While the form of the invention illustrated is a continuous flow-through process, the invention is equally applicable to batch processing.

Advantages of the device disclosed herein include the use of a matrix with
  (a) a high surface area;
  (b) transparency to the light throughout all areas of the matrix and hence effective utilization of the light by the photoreactive material;
  (c) a high porosity and hence a low fluid pressure drop;
  (d) an effective turbulent mixing of the contaminated fluid as it passes through the matrix in contact with the photoreactive material; and
  (e) good resistance to clogging, due to the use of an open mesh-like structure, in contrast to a filter with much smaller holes.

We claim:

1. A matrix for use in a method of removing, reducing or detoxifying organic pollutants from a fluid, characterized by a porous substrate having a photoreactive metal semiconductor material bonded with, to or into surfaces of said substrate, said substrate comprising a filamentous, fibrous or stranded base material through which the fluid can flow in intimate contact with the photoreactive material.

2. A matrix according to claim 1, wherein the substrate is at least partially transparent to light at a wavelength to which the semiconductor material photoreacts.

3. A matrix as in claim 2, wherein the substrate comprises a plurality of superposed sheets of said base material in the form of a mesh.

4. A matrix as in claim 2, wherein the substrate comprises a mesh of said base material wound into a cylindrical, multi-convolution sleeve.

5. A matrix as in claim 2, 3 or 4, wherein the substrate is in the form of a mesh.

6. A matrix as in claim 2, 3 or 4 wherein the base material is fiberglass.

7. A matrix as in claim 2, 3 or 4, wherein the substrate is fiberglass in the form of a mesh.

8. A matrix as in claim 1, 2 or 3 wherein the photoreactive material is anatase.

9. A matrix as in claim 1, 2 or 3, wherein the photoreactive material is selected from CdS, CdSe, $ZnO_2$, $WO_3$ and $SnO_2$.

10. A matrix as in claim 1, 2 or 3, wherein the photoreactive material includes an enhancing dopant.

11. A matrix as in claim 1, 2 or 3, wherein the photoreactive material includes platinum as a dopant.

12. A matrix for use in a method of removing, reducing or detoxifying organic pollutants from a fluid, comprising a substrate in the form of a porous mesh of fiberglass wound into a cylindrical multi-convolution sleeve through which the fluid can flow in intimate contact with surface of said substrate, and a photoreactive metal semiconductor material bonded with, to or into said surfaces.

13. A matrix for use in a method of removing, reducing or detoxifying organic pollutants from a fluid, comprising a substrate having a photoreactive metal semiconductor material bonded with, to or into surfaces of said substrate, said substrate comprising at least one porous tube coated with said photoreactive material, said tube being of perforated glass or in the form of a perforated film whereby the fluid can flow through said substrate in intimate contact with the photoreactive material.

14. A matrix according to claim 12 or 13, wherein the substrate is at least partially transparent to light at a wavelength to which the semiconductor material photoreacts.

15. A matrix according to claim 13, wherein said substrate comprises at least two coaxial tubes of film or glass coated with said photoreactive material.

16. A matrix according to claim 2, wherein said transparency of the substrate is the result of at least one of
    (a) the base material being substantially transparent to light at said wavelength, and
    (b) the porous nature of the substrate permitting the transmission of light therethrough.

17. A matrix according to claim 12 or 13, wherein the substrate is at least partially transparent to light at a wavelength to which the semiconductor material photoreacts, and wherein said transparency of the substrate is the result of at least one of
    (a) the base material being substantially transparent to light at said wavelength, and
    (b) the porous nature of the substrate permitting the transmission of light therethrough.

18. A matrix as in claim 13, 14 or 15, wherein the photoreactive material is anatase.

19. The combination of a matrix according to claim 1, 12 or 13, with a source of light for irradiating the matrix, said light being of a wavelength to activate the photoreactive material, and means for flowing a fluid through the matrix during such irradiation.

20. A device for removing, reducing or detoxifying organic pollutants from a fluid comprising
    (a) a jacket having an inlet and an outlet,
    (b) a matrix located in the jacket,
    (c) the matrix comprising a porous substrate having surfaces with, to or into which a photoreactive metal semiconductor material is bonded, whereby in travelling from the inlet to the outlet a fluid flows through the matrix in intimate contact with the photoreactive material, and
    (d) means for exposing said photoreactive material to light of a wavelength to activate the same.

21. A device according to claim 20, wherein said means (d) is a lamp in said jacket.

22. A device according to claim 20, wherein said means (d) comprises material transparent to said light for allowing said light to enter the jacket from the exterior thereof.

23. A device according to claim 22, in combination with a lamp located outside the jacket for generating said light.

24. A device for removing, reducing or detoxifying organic pollutants from a fluid comprising
    (a) a jacket having an inlet and an outlet,
    (b) a cylindrical lamp mounted in the jacket for generating light,
    (c) a matrix comprising a substrate in the form of a multi-convolution sleeve of mesh surrounding the lamp and located in the jacket,
    (d) the substrate having surfaces with, to or into which photoreactive metal semiconductor material is bonded, whereby in travelling from the inlet to the outlet a fluid flows through the matrix in intimate contact with the photoreactive material, and
    (e) the light being of a wavelength to activate this photoreactive material.

25. A device according to claim 20, 21 or 24 wherein the photoreactive material is anatase.

26. A device according to claim 20, 21 or 24, wherein the photoreactive material is selected from CdS, CdSe, $ZnO_2$, $WO_3$ and $SnO_2$.

27. A device according to claim 20, 21 or 24, wherein the photoreactive material includes an enhancing dopant.

28. A device according to claim 20, 21 or 24, wherein the substrate is formed of fiberglass mesh.

* * * * *